United States Patent [19]

Oshiro et al.

[11] 4,219,014

[45] Aug. 26, 1980

[54] LIGHT SOURCE DEVICE FOR ENDOSCOPE WHICH CONTROLS THE VOLTAGE ACROSS A SINGLE LIGHT SOURCE FOR PERFORMING BOTH ILLUMINATION AND PHOTOGRAPHY

[75] Inventors: Susumu Oshiro, Iwatsuki; Morihiko Yoshida, Urawa, both of Japan

[73] Assignee: Fuji Photo Optical Co., Ltd., Omiya, Japan

[21] Appl. No.: 817,133

[22] Filed: Jul. 20, 1977

[51] Int. Cl.² ........................ A61B 1/04; G03B 29/00
[52] U.S. Cl. ........................................ 128/6; 354/62
[58] Field of Search ............... 128/6, 7, 8, 9, 11, 128/3–5; 358/98; 354/62, 63, 32, 33, 60 F, 126

[56] References Cited

U.S. PATENT DOCUMENTS 3,329,074 7/1967 Gosselin ............................ 354/62
4,086,583 4/1978 Takahashi ............................ 354/62

Primary Examiner—Robert W. Michell
Assistant Examiner—Jeffrey W. Tayon

[57] ABSTRACT

A light source provided in an endoscope is controlled to provide a constant comparatively low luminance when the object is to be observed, and to provide a first lowered and then gradually increased luminance when the object is to be photographed. The voltage and consequently, the luminance is first further lowered below the comparatively low luminance for observation when the object is to be photographed and the voltage is then increased so that a high luminance results. A control circuit is connected between a shutter release signal generating circuit and a light source to control the voltage across the light source upon receipt of the shutter release signal.

5 Claims, 6 Drawing Figures

F I G. I
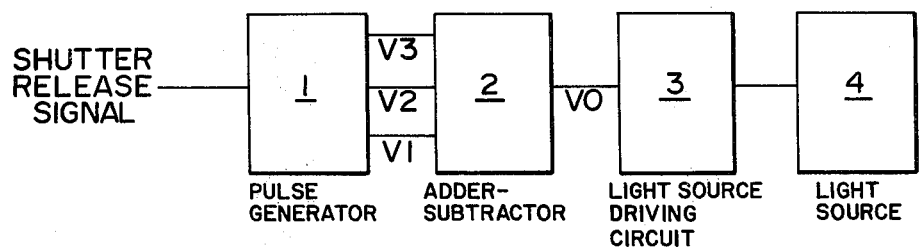
F I G. 2
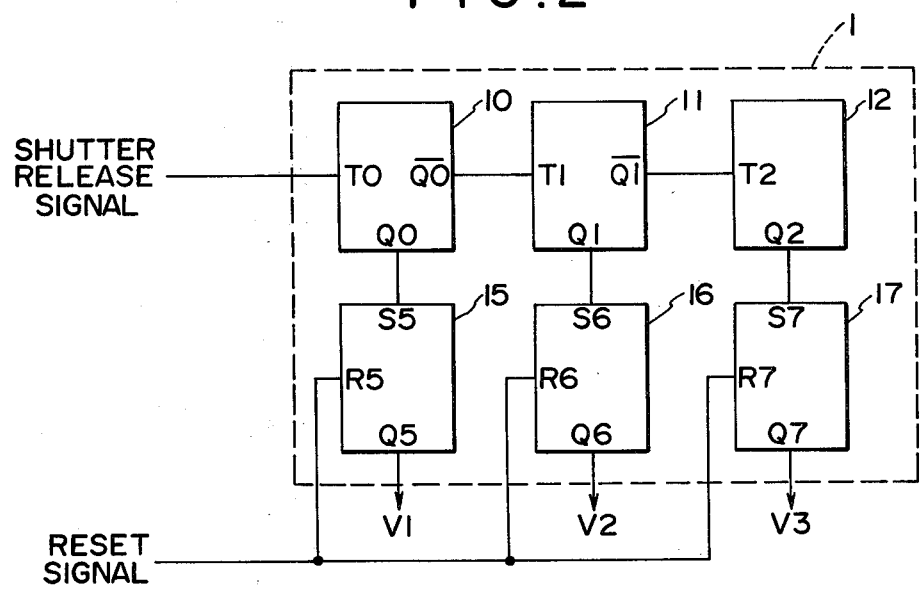
F I G. 3
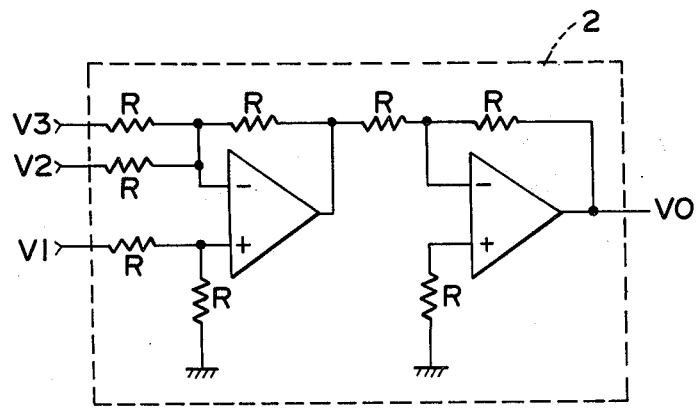

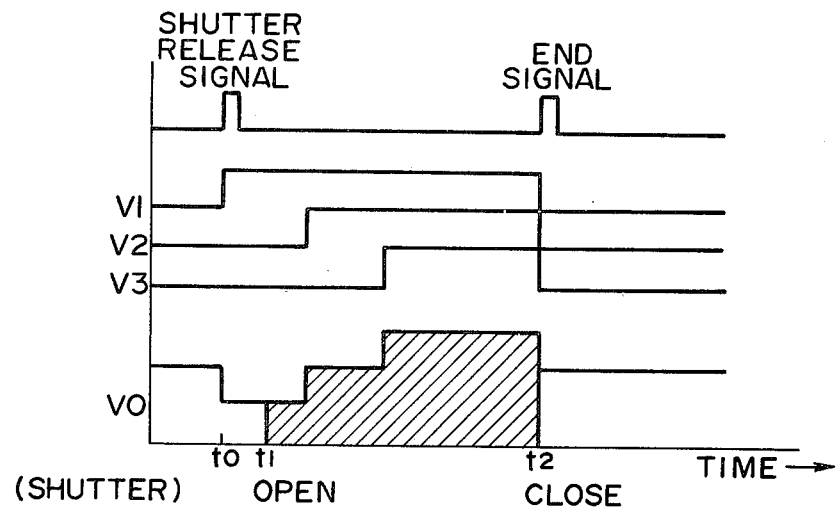
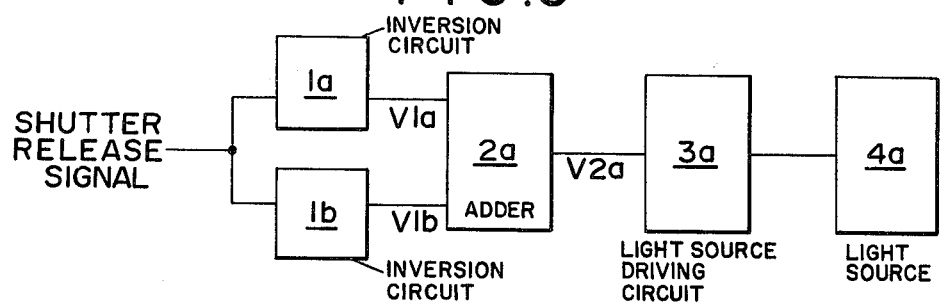
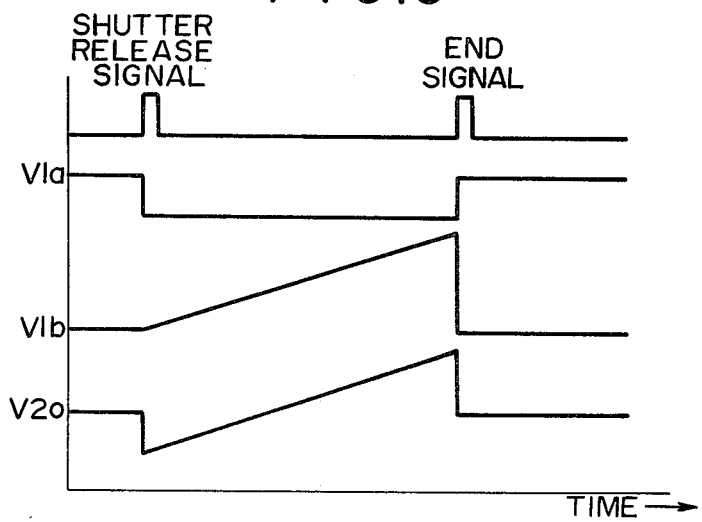

LIGHT SOURCE DEVICE FOR ENDOSCOPE WHICH CONTROLS THE VOLTAGE ACROSS A SINGLE LIGHT SOURCE FOR PERFORMING BOTH ILLUMINATION AND PHOTOGRAPHY

BACKGROUND OF THE INVENTION

1. Field of the Invention

This invention relates to a light source device for an endoscope, and more particularly to an improvement in a light source for an endoscope which is used for illuminating the object to be observed and/or photographed by the endoscope.

2. Description of the Prior Art

In the conventional endoscope, it has been known to provide a low luminance illumination when observing the object such as the human stomach and intestines and the like in order not to cause an ulcer by the heat of the light source and to provide a high luminance illumination when taking a photograph of the observed object. When providing the high luminance illumination, a switch is operated to illuminate the object only for a very short time. In this type of conventional endoscope, it is technically very difficult to make the switching operation of the illumination synchronize with the release of the shutter, since the rising characteristic of the illumination is not completely constant. In the endoscope of this type, a camera which determines the shutter speed based on the brightness of the object illuminated by the light source which is measured by integrating the quantity of light reflected by the surface of the film therein, is often used. In this case, it is also difficult to have the start of the integration of the light perfectly synchronize with the start of release of the shutter.

In view of the above problem, it has been proposed to provide a diaphragm in front of the light source of the endoscope to control the illumination without changing the luminance of the light source. In this case, the light source is constantly turned on to provide illumination of high luminance and the diaphragm is operated to stop down the aperture thereof when the object is observed and fully open the aperture thereof when the object is photographed. Further, the diaphragm is closed before the shutter is released and is opened when the shutter is completely opened. The endoscope with the above described diaphragm is advantageous over said conventional endoscope in that the rising characteristic of the illumination does not influence the exposure. However, this kind of endoscope with the diaphragm has a defect in that time is wasted between the initiation of the shutter release and the actual release of the shutter during which the diaphragm is mechanically operated.

The above described endoscope provided with a diaphragm has a further defect as follows. Since the luminance of the light source is constant and the diaphragm is fully opened when the object is photographed, the exposure time is made longer when an object far from the light source of the endoscope is photographed than when an object close thereto is photographed. Therefore, in order to obtain a sharp picture even for the object far from the endoscope, the exposure time is desired to be made as short as possible for the object far from the endoscope. Accordingly, the luminance of the light source is made high. Consequently, the shutter speed of the camera should be made very high for the object close to the endoscope. From a technical viewpoint, it is practically very difficult to obtain such a high shutter speed with a sufficient preciseness and to precisely make the shutter release of such a high speed synchronize with said start of integration of light or operation of the diaphragm.

SUMMARY OF THE INVENTION

In view of the above defects inherent in the conventional endoscopes, the primary object of the present invention is to provide a light source device for an endoscope in which a constant low illumination is obtained for observation of the object and a high illumination is obtained for photographing the object and aforesaid defects caused by the failure in synchronization between the start of release of the shutter and the start of integration of the light measured are eliminated.

Another object of the present invention is to provide a light source device for an endoscope in which the exposure time can be made short even for an object far from the endoscope.

Still another object of the present invention is to provide a light source device for an endoscope in which the object close to the endoscope can be photographed with a shutter speed which is not so high and accordingly can easily be obtained.

The above objects of the present invention can be accomplished by providing a constant luminance of illumination for observation of the object and making the luminance lower once and then gradually increasing the luminance when photographing. Upon receipt of a shutter release signal, the illumination lowers the luminance thereof and then increasing the same gradually. Since the object can be observed with a constant luminance of proper level, there is no fear of making an ulcer in the human intestines or the like. Further, when photographing the object, the luminance is first lowered and then increased to a high level. Thus, since the luminance is low at the initial stage of the shutter release, the error in synchronization between the start of the shutter release and the start of the integration of the light measured does not substantially affect the resulting exposure. Besides, since the luminance is increased to a great extent during the time the shutter is opened, a sufficiently high luminance is obtained to photograph an object far from the endoscope with a proper shutter speed. When the object is close to the endoscope, the shutter speed is determined fast by the automatic exposure control means in the camera. However, since the luminance is low at the initial stage of the exposure, the shutter speed is not controlled to be so high. Thus, photographing can be conducted with a proper exposure time not only for the object far from the endoscope but also for the object close thereto.

BRIEF DESCRIPTION OF THE DRAWING

FIG. 1 is a block diagram of a circuitry employed in the light source device in accordance with the present invention, FIG. 2 is a circuit view showing a pulse generator used in the circuitry of FIG. 1, FIG. 3 is a circuit view showing an adder-subtractor which is used in the circuitry of FIG. 1, FIG. 4 is a time chart showing the terminal outputs of the circuitry shown in FIG. 1, FIG. 5 is a block diagram of a circuitry employed in the light device in accordance with another embodiment of the present invention, and FIG. 6 is a time chart showing the terminal outputs of the circuitry shown in FIG. 5.

DESCRIPTION OF THE PREFERRED EMBODIMENTS

An embodiment of the circuitry employed in the light source device of the present invention is shown in FIG. 1. Referring to FIG. 1, a shutter release signal is put into a pulse generator 1 comprising monostable multivibrators 10, 11 and 12 and flip-flops 15, 16 and 17 as shown in FIG. 2. The pulse generator 1 gives three outputs V1, V2 and V3, which are put into an adder-subtractor 2 which constitutes a staircase generator together with said pulse generator 1. The staircase output V0 of the staircase generator 1 and 2 is put into a light source driving circuit 3 which amplifies the power of the output of the adder-subtractor 2 to control the light source 4 connected therewith.

The pulse generator 1 is comprised of three monostable multivibrators 10, 11 and 12 respectively having input terminals T0, T1 and T2 and output terminals Q0, Q1 and Q2. The first and second monostable multivibrators 10 and 11 have additional output terminals $\overline{Q0}$ and $\overline{Q1}$ to be connected with the input terminals T1 and T2 of the second and third monostable multivibrators 11 and 12. The pulse generator 1 is further comprised of three flip-flops 15, 16 and 17, which are S-R flip-flops having input terminals S5, S6 and S7 to be connected with the output terminals Q0, Q1 and Q2 of the monostable multivibrators 10, 11 and 12. The outputs Q5, Q6 and Q7 of the flip-flops 15, 16 and 17 are connected with the adder-subtractor 2 as shown in FIG. 3, and the reset terminals R5, R6 and R7 of the flip-flops 15, 16 and 17 are connected with the input of a reset signal such as an end signal of the exposure time. The input terminal T0 of the first monostable multivibrator 10 is connected with the input of a shutter release signal.

The adder-subtractor 2 is well known in the art, and accordingly the operation thereof is not described in detail here. The arithmetic operation thereof is represented by the formula $V0 = -V1 + V2 + V3$.

The operation of the circuitry as shown in FIG. 1 and described hereinabove will be described hereinbelow with reference to FIG. 4. When a shutter release signal from the shutter release means (not shown) of a camera of the endoscope is put into the pulse generator 1, the first monostable multivibrator 10 is inversed and the level at the output terminal Q0 thereof becomes high ("H") level. The H-level output of the first monostable multivibrator 10 puts the set terminal S5 of the S-R flip-flop 15 into H-level, and the output terminal Q5 (V1) thereof maintains H-level until a H-level is given to the reset terminal R5.

Then, when a predetermined time, e.g. 15 msec, has passed, said monostable mulitvibrator 10 is recovered of its original state to inverse the next monostable multivibrator 11 and puts the output level of the output terminal Q1 into H-level. Thus, similarly to the above operation, the output terminal Q6 of the second flip-flop 16 maintains its output level (V2) in H-level.

Similarly, the output terminal Q7 (V3) of the third flip-flop 17 maintains H-level when another predetermined time has passed thereafter. The above operation, namely the change in the output level of the three output levels V1, V2 and V3 is shown in FIG. 4.

These outputs are operated through the adder-subtractor 2 according to said formula and the staircase output V0 is obtained at the output of the adder-subtractor 2. The staircase output V0 is power amplified by the light source driving circuit 3 and the output of the circuit 3 controls the luminance of the light source 4.

Therefore, it needs a time of 5 to 15 msec after the shutter release signal has been received (t0) until the shutter is actually opened (t1), and accordingly it becomes difficult to precisely make the start of control of the light source synchronize with the start of integration of light by the light measuring circuit of the automatic exposure control circuit. However, since the luminance of the light source is very low initially, the error n synchronization does not affect the result of the exposure control.

Then, the integrating circuit operates to measure the scene brightness and an end signal is generated when the exposure is completed. The structure and operation of the automatic exposure control system are well known in the art and is not the subject matter of the present invention, and accordingly, the detailed description thereof is omitted here.

By the end signal generated from the automatic exposure control circuit, the reset terminals R5, R6 and R7 of the S-R flip-flops 15, 16 and 17 are put into H-level and the flip-flops are recovered of their initial state and the light source 4 is put into its original state to emit light of low luminance suitable for observation, and the next shutter release operation is made possible.

Although the staircase output V0 is generated by use of a pulse generator 1 and an adder-subtractor 2, it will be noted by those skilled in the art that the staircase output could be obtained by other staircase generators such as a combination of a flip-flop, a ladder network, several constant voltage circuits and gate circuits.

FIG. 5 shows another embodiment of the present invention wherein a circuitry to control a light source 4a is comprised of an inversion circuit 1a, an integrating circuit 1b connected in parallel with the inversion circuit 1a, an adder 2a connected with the outputs of said two circuits 1a and 1b to provide a gradually increasing output, and a light source driving circuit 3a which amplifies the power of the increasing output of the adder 2a.

The operation of the above described circuitry as shown in FIG. 5 will be described hereinbelow with reference to the time chart shown in FIG. 6. When a shutter release signal is first put into the inversion circuit 1a and the integrating circuit 1b, the inversion circuit 1a generates an output V1a of low level ("L" level) and the integrating circuit 1b generates an output V1b which gradually increases as shown in FIG. 6. These outputs are added together by the adder 2a and an output V2a which is first lowered and then gradually increased is obtained. Therefore, the light source 4a is controlled in the same manner as that effected in the first embodiment. Although in the first embodiment the luminance of the light source 4 is controlled stepwise, in the second embodiment it is controlled linearly.

In both the embodiments, it is desired that the luminance of the light source is lowered to such an extent that the change in luminance does not affect the result of integration and the lowering of the luminance does not affect the rising characteristic of the light source.

We claim:

1. A light source device for an endoscope which is used for both observation and photographing, comprising a light source and a light source control means, said light source control means being connected between a shutter release signal generating means in a camera of the endoscope and said light source, said light source control means including means for generating a constant low voltage output to thereby effect a constant low luminance of the light source when the endoscope is used for observation, said light source control means also including means for generating upon receipt of said shutter release signal from the shutter release signal generating means a voltage output lower than said constant low voltage output which first lowers the luminance of the light source from said constant low luminance down to a lower but non-zero level until after the shutter is opened and for generating a voltage which gradually increases the luminance up to a level higher than the level of said constant low luminance for completing the photographic operation.

2. A light source device for an endoscope as defined in claim 1 wherein said light source control means includes a staircase voltage generator for changing the level of the luminance stepwise.

3. A light source device for an endoscope as defined in claim 2 wherein said staircase voltage generator comprises a pulse generator and an adder-subtractor.

4. A light source device for an endoscope as defined in claim 1 wherein said light source control means includes an integrator for varying the level of the luminance linearly.

5. A light source device for an endoscope as defined in claim 4 wherein said light source control means comprises an inversion circuit for generating an output signal of a relatively low level and an integrator circuit for generating an output signal of increasing level, said two circuits being arranged in parallel with respect to each other and connected to said shutter release signal generating means, and an adder connected with said inversion circuit and said integrator circuit for adding the outputs thereof.

* * * * *